United States Patent [19]

Andrianov et al.

[11] Patent Number: 5,494,673
[45] Date of Patent: Feb. 27, 1996

[54] PHOSPHAZENE POLYELECTROLYTES AS IMMUNOADJUVANTS

[75] Inventors: Alexander K. Andrianov, Belmont; Sharon A. Jenkins, Peabody; Lendon G. Payne, Arlington; Bryan E. Roberts, Cambridge, all of Mass.

[73] Assignee: Virus Research Institute, Cambridge, Mass.

[21] Appl. No.: 273,285

[22] Filed: Jul. 11, 1994

Related U.S. Application Data

[63] Continuation-in-part of Ser. No. 90,841, Jul. 12, 1993.
[51] Int. Cl.$^6$ .......................... A61K 39/39; A61K 39/29; A61K 39/02; A61K 29/145
[52] U.S. Cl. ................... 424/280.1; 424/227.1; 424/234.1; 424/209.1
[58] Field of Search ................ 424/280.1, 208.1, 424/227.1, 499, 497, 193.1, 199.1, 204.1, 234.1, 93.1, 93.4, 93.6, 256.1, 209.1

[56] References Cited

U.S. PATENT DOCUMENTS

| | | |
|---|---|---|
| 3,893,980 | 7/1975 | Allcock et al. . |
| 4,026,839 | 5/1977 | Dieck et al. . |
| 4,055,520 | 10/1977 | Dieck et al. . |
| 4,073,824 | 2/1978 | Dieck et al. . |
| 4,073,825 | 2/1978 | Dieck et al. . |
| 4,094,971 | 6/1978 | Chedid et al. . |
| 4,209,014 | 6/1980 | Sefton . |
| 4,353,888 | 10/1982 | Sefton . |
| 4,440,921 | 4/1984 | Allcock et al. . |
| 4,451,647 | 5/1984 | Allcock et al. . |
| 4,495,174 | 1/1985 | Allcock et al. . |
| 5,126,147 | 6/1992 | Silvestri et al. ............... 424/497 |
| 5,149,543 | 9/1994 | Cohen et al. ............... 424/499 |

*Primary Examiner*—Kay K. A. Kim
*Attorney, Agent, or Firm*—Elliot M. Olstein

[57] ABSTRACT

An immunoadjuvant soluble polyphosphazene polyelectrolyte is disclosed. In one embodiment, the polymeric adjuvant is an poly(organophosphazene) with (i) ionized or ionizable pendant groups that contain, for example, carboxylic acid, sulfonic acid, or hydroxyl moieties, and (ii) pendant groups that are susceptible to hydrolysis under the conditions of use, to impart biodegradability to the polymer.

18 Claims, No Drawings

PHOSPHAZENE POLYELECTROLYTES AS IMMUNOADJUVANTS

This application is a continuation-in-part of U.S. application Ser. No. 08/090,841 filed on Jul. 12, 1993.

BACKGROUND OF THE INVENTION

This application is in the area of polymers for biomedical applications, and in particular describes polymers that can be used as immunoadjuvants.

VACCINE DEVELOPMENT

A wide variety of antigens stimulate the production of antibodies in animals and confer protection against subsequent infection. However, some antigens are unable to stimulate an effective immune response.

The immunogenicity of a relatively weak antigan is often enhanced by the simultaneous administration of the antigen with an adjuvant, a substance that is not immunogenic when administered alone, but will induce a state of mucosal and/or systemic immunity when combined with the antigen. It has been traditionally thought that adjuvants, such as mineral oil emulsions or aluminum hydroxide, form an antigen depot at the site of injection that slowly releases antigen. Recent studies by Allison and Byars, in: "Vaccines: New Approaches to Immunological Problems:, R. W. Ellis, ed., p. 431, Butterworth-Heinemann, Oxford (1992) indicate that adjuvants enhance the immune response by stimulating specific and sometimes very narrow branches of the immune response by the release of cytokines. Unfortunately, many immunoadjuvants, such as Freund's Complete Adjuvant, are toxic and are therefore only useful for animal research purposes, not human vaccinations. Freund's Complete Adjuvant contains a suspension of heat-killed Mycobacterium tuberculosis in mineral oil containing a surfactant and causes granulomatous lesions in animals at the site of immunization. Freund's adjuvant may also cause the recipient of a vaccine to test positive for tuberculosis.

Some synthetic polyelectrolytes have been found to provide immunostimulation when combined with an antigen. For example, the adjuvant activity of polyacrylic acid (PAA), copolymers of acrylic acid and N-vinylpyrrolidone (CP-AAVPD), poly-2-methyl-5-vinyl pyridine (PMVP), poly-4-vinylN-ethylpyridinium bromide (PVP-R$_2$) and similar compounds, when conjugated to an antigen, has been studied by Petrov et. al., Jhurnal Vses. Khim. Ob-va im. D. I. Mendeleeva, 33:22–42 (1988). The immunomodulatory effect of polyelectrolyte complexes containing many of these same polyelectrolytes has also been more recently reviewed by Petrov, et al., Sov. Med. Rev. D. Immunol., 4:1–113 (1992). However, the toxicity and biodegradability of these polymers has not been studied and may prevent use of these polymers as adjuvants for use in humans.

A non-toxic adjuvant or carrier having the ability to stimulate an immune response to non-antigenic or weakly antigenic molecules would be useful in the development and administration of vaccines.

Therefore, it is an object of the present invention to provide an adjuvant that can be safely administered to humans and animals with minimal toxicity.

It is a further object of the present invention to provide an adjuvant that is soluble and biodegradable.

It is a further object of the present invention to provide a vaccine that confers protection against an organism such as the influenza virus or *Clostridium tetani* bacteria.

It is a further object of the present invention to provide a rapid and efficient method of synthesizing a polymer, such as polyphosphazene, for use as an adjuvant.

SUMMARY OF THE INVENTION

A synthetic, water-soluble polyphosphazene is disclosed for use as an adjuvant. In a preferred embodiment, the phosphazene is a polyelectrolyte that is biodegradable and that exhibits minimal toxicity when administered to animals, such as humans.

In one embodiment, the polymeric adjuvant is an poly(organophosphazene) with (i) ionized or ionizable pendant groups that contain, for example, carboxylic acid, sulfonic acid, or hydroxyl moieties, and (ii) pendant groups that are susceptible to hydrolysis under the conditions of use, to impart biodegradability to the polymer. Suitable hydrolyzable groups include, for example, chlorine, amino acid, amino acid ester, imidazole, glycerol, and glucosyl.

Two examples of polyphosphazenes that are useful as immunoadjuvants are poly[di(carboxylatophenoxy)phosphazene-co-di(glycinato)phosphazene-co(carboxylatophenoxy)(glycinato)phosphazene] and poly[di(carboxylatophenoxy) phosphazene-co-di(chloro)phosphaz ene-co-(carboxylatophenoxy)-(chloro)phosphazene].

A vaccine composition is prepared by either mixing or conjugating the polymer adjuvant with an antigen prior to administration. Alternatively, the polymer and antigen can be administered separately to the same site.

When cross-linked with a multivalention, the polymer becomes less soluble, resulting in slower release of the polymer from the site of administration.

DETAILED DESCRIPTION OF THE INVENTION

The term amino acid, as used herein, refers to both natural and synthetic amino acids, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl. The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a C2 to C20 straight or branched hydrocarbon with at least one double or triple bond, respectively. The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(lower alkyl), —CO$_2$H, —SO$_3$H, —PO$_3$H, —CO$_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "pharmaceutically acceptable cation" refers to an organic or inorganic moiety that carries a positive charge and that can be administered as a countercation in a phosphazene polyelectrolyte.

The term heteroalkyl, as used herein, refers to a alkyl group that includes a heteroatom such as oxygen, sulfur, or nitrogen (with valence completed by hydrogen or oxygen) in the carbon chain or terminating the carbon chain.

A synthetic polymer is provided for use as an immunoadjuvant. The polymer adjuvant is a polyphosphazene that is at least partially soluble in water (typically to an extent of at least 0.001% by weight), an aqueous buffered salt solution, or aqueous alcohol solution. The polyphosphazene preferably contains charged side groups, either in the form of an acid or base that is in equilibrium with its counter ion, or in the form of an ionic salt thereof.

The polymer is preferably biodegradable and exhibits minimal toxicity when administered to animals, including humans.

SELECTION OF POLYPHOSPHAZENE POLYELECTROLYTES.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

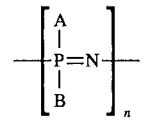

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)aminoincluding alkylamino-, heteroaralkyl, di(aliphatic)amino- including dialkylamino-, arylamino-, diarylamino-, alkylarylamino-, -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic)PO$_3$H, and -oxy(aliphatic)hydroxyl, including oxy(alkyl)hydroxyl; -oxyalkaryl, -oxyaralkyl, -thioaryl, thioaliphatic including -thioalkyl, -thioalkaryl, thioaralkyl, —NHC(O)O-(aryl or aliphatic), —O—[(CH$_2$)xO]y—CH$_2$)—O—[(Ch$_2$)xO]y(CH$_2$)xNH(CH$_2$)xSO$_3$H, and —O—[(CH$_2$)xO]y-(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

In one embodiment, the immunoadjuvant is a biodegradable polyphosphazene of the formula:

wherein A and B can vary independently in the polymer, and can be:

(i) a group that is susceptible to hydrolysis under the conditions of use, including but not limited to chlorine, amino acid, amino acid ester (bound through the amino group), imidazole, glycerol, or glucosyl; or (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic)aminoincluding dialkylamino-, arylamino-, diarylamino-, alkylarylamino-, oxyaryl including but not limited to -oxyphenylCO$_2$H, -oxyphenyl SO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy (aliphatic)PO$_3$H, and -oxy(aliphatics)hydroxyl, including -oxy(alkyl) hydroxyl; -oxyalkaryl, -oxyaralkyl, -thioaryl, -thioaliphatic including -thioalkyl, -thioalkaryl, or thioaralkyl;

wherein the polymer contains at least one percent or more, preferably 10 percent or more, and more preferably 80 to 90 percent or more, but less than 100%, of repeating units that are not susceptible to hydrolysis under the conditions of use, and wherein n is an integer of 4 or more, and preferably between 10 and 20,000 to 300,000.

It should be understood that certain groups, such as heteroaromatic groups other than imidazole, hydrolyze at an extremely slow rate under neutral aqueous conditions, such as that found in the-blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer.

In other embodiments, the immunoadjuvant is: (i) a nonbiodegradable polyphosphazene wherein none, or virtually none, of the pendant groups in the polymer are susceptible to hydrolysis under the conditions of use, or (ii) a completely biodegradable polyphosphazene wherein all of the groups are susceptible to hydrolysis under the conditions of use (for example, poly[di(glycinato)phosphazene]).

Phosphazene polyelectrolytes are defined herein as polyphosphazenes that contain ionized or ionizable pendant groups that render the polyphosphazene anionic, cationic or amphophilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte immunoadjuvant contains pendant groups that include carboxylic acid, sulfonic acid, or hydroxyl moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

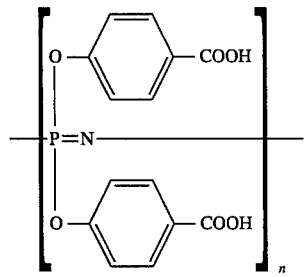

wherein n is an integer, preferably an integer between 10 and 10,000 to 300,000. This polymer has the chemical name poly[di(carboxylatophenoxy)phosphazene] or, alternatively, poly[bis(carboxylatophenoxy)phosphazene] (PCPP).

The phosphazene polyelectrolyte is preferably biodegradable to prevent eventual deposition and accumulation of polymer molecules at distant sites in the body, such as the spleen. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C.

Most preferably the polymer is a poly(organophosphazene) that includes pendant groups that include carboxylic acid moieties that do not hydrolyze under the conditions of use and pendant groups that are susceptible to hydrolysis under the conditions of use. Examples of preferred phosphazene polyelectrolytes with hydrolysis-sensitive groups are poly[di(carboxylatophenoxy)phosphazene-co-di(amino acid)phosphazene-co-(carboxylatophenoxy)(amino acid)phosphazene], specifically including poly[di(carboxylatophenoxy)phosphazene-co-di(glycinato)phosp hazene-co-(carboxylatophenoxy)(glycinato)phosphazene], and poly[di(carboxylatophenoxy)phosphazene-co-di(chloro)phosphaz ene-co-(carboxylatophenoxy)(chloro)phosphazene].

The toxicity of the polyphosphazene determined using cell culture experiments well known to those skilled in the art. For example, toxicity of poly[di(carboxylatophenoxy) phosphazene] was determined in cell culture by coating cell culture dishes with the poly[di(carboxylatophenoxy) phosphazene]. Chicken embryo fibroblasts were then seeded onto the coated petri dishes. Three days after seeding the chicken embryo fibroblasts, the cells had become flattened and spindles formed. Under phase contrast microscopy, mitotic figures were observed. These observations provide evidence of the non-toxicity of poly[di(carboxylatophenoxy)phosphazene] to replicating cells.

Crosslinked polyphosphazenes for use as immunoadjuvants can be prepared by combining a phosphazene polyelectrolyte with a metal multivalent cation s~uch as zinc, calcium, bismuth, barium, magnesium, aluminum, copper, cobalt, nickel, or cadmium.

SYNTHESIS OF PHOSPHAZENE POLYELECTROLYTES

Polyphosphazenes, including phosphazene polyelectrolytes, can be prepared by a macromolecular nucleophilic substitution reaction of poly(dichloro phosphazene) with a wide range of chemical reagents or mixture of reagents in accordance with methods known to those skilled in the art. Preferably, the phosphazene polyelectrolytes are made by reacting the poly(dichloro phosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly(dichlorophosphazene) and the reaction conditions as necessary. Preferred polyphosphazenes for immunoadjuvant activity have a molecular weight of over 1,000.

For example, poly[(carboxylatophenoxy)(glycinato) phosphazene] (PC-GIPP) is prepared by the nucleophilic substitution reaction of the chlorine atoms of the poly(dichlorophosphazene) with propyl phydroxybenzoate and ethyl glycinate hydrochloride (PC-G1PP synthesis). The poly[(aryloxy)(glycinato)phosphazene] ester thus obtained is then hydrolyzed to the corresponding poly(carboxylic acid). Other polyphosphazenes can be prepared as described by Allcock, H. R.; et al., Inorg. Chem. 11, 2584 (1972); Allcock, H. R.; et al., Macromolecules 16, 715 (1983);Allcock, H. R.; et al., Macromolecules 19,1508

(1986); Allcock, H. R.; et al., Biomaterials 19, 500 (1988); Allcock, H. R.; et al., Macromolecules 21, 1980 (1988); Allcock, H. R.; et al., Inorg. Chem. 21(2), 515521 (1982); Allcock, H.R.; et al., Macromolecules 22:7579 (1989); U.S. Pat. Nos. 4,440,921, 4,495,174, 4,880,622 to Allcock, H.R.; et al.,; U.S. Pat. No. 4,946,938 to Magill, et al., U.S. Pat. No. 5,149,543 to Cohen et al., and the publication of Grolleman, et al., J. Controlled Release 3,143 (1986), the teachings of which, and polymers disclosed therein, are incorporated by reference herein.

SELECTION OF AN ANTIGEN

The antigan can be derived from a cell, bacteria, or virus particle, or portion thereof. As defined herein, antigan may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell mediated. In the event the material to which the immunogenic response is to be directed is poorly antigenic, it may be conjugated to a carrier such as albumin or to a hapten, using standard covalent binding techniques, for example, with one of the several commercially available reagent kits.

In one embodiment, the polymer is used to deliver nucleic acid which encodes antigen to a mucosal surface where the nucleic acid is expressed.

Examples of preferred antigens include viral proteins such as influenza proteins, human immunodeficiency virus (HIV) proteins, and hepatitis B proteins, and bacterial proteins and lipopolysaccharides such as gram negative bacterial cell walls and Neisseria gonorrhea proteins.

PREPARATION OF AN IMMUNOGENIC COMPOSITION

Combining Antigen with polymer for simultaneous administration.

An immunogenic composition, or vaccine, is prepared by combining the polymer adjuvant with an antigen. Approximately 0.5–0.0001 parts of antigen is added to one part polymer, preferably by stirring a solution of polymer and antigen until a solution or suspension is obtained, preferably for 10 minutes or more at 25° C. The polymer is preferably combined with the antigen using a method dispersing the antigen uniformly throughout the adjuvant. Methods for liquifying the polymer include dissolving the polymer in an aqueous-based solvent, preferably having a pH range of between 7.1 and 7.7, and melting the polymer. The latter is useful only when the antigen is stable at the polymer melting temperature. The antigan is then mixed with the polymer. The polymer and the antigen, in solid form, for example, when the antigen is lyophilized, can also be physically mixed together, for example, by compression molding. The polymer can also be used to encapsulate the antigen, for example, using the method of U.S. Pat. No. 5,149,543 to Cohen, et al., the teachings of which are incorporate herein, or by spray drying a solution of polymer and antigen. Alternatively, microspheres containing the antigen and adjuvant can be prepared by simply mixing the components in an aqueous solution, and then coagulating the polymer together with the substance by mechanical forces to form a microparticle. The microparticle can be stabilized, if necessary or desired, using electrolytes, pH changes, organic solvents, heat or frost to form polymer matrices encapsulating biological material.

In a preferred embodiment, approximately one part of polymer is dissolved in 10 parts 3% $Na_2CO_3$ aqueous solution while stirring, then 10 to 90 parts phosphate buffer pH 7.4 is slowly added.

POLYMER—ANTIGEN CONJUGATES

The polymer can also be covalently conjugated with the antigen to create a water-soluble conjugate in accordance with methods well-known to those skilled in the art, usually by covalent linkage between an amino or carboxyl group on the antigen and one of the ionizable side groups on the polymer.

CROSS-LINKED POLYMER ADJUVANT

In an alternative preferred embodiment, the polymer is cross-linked with a multivalent ion, preferably using an aqueous solution containing multivalent ions of the opposite charge to those of the charged side groups of the polyphosphazene, such as multivalent cations if the polymer has acidic side groups or multivalent anions if the polymer has basic side groups.

Preferably, the polymers are cross-linked by di and trivalent metal ions such as calcium, copper, aluminum, magnesium, strontium, barium, tin, zinc, and iron, organic cations such as poly(amino acid)s, or other polymers such as poly(ethyleneimine), poly(vinylamine) and polysaccharides.

ADDITIVES TO THE POLYMER—ADJUVANT MIXTURE.

It will be understood by those skilled in the art that the immunogenic vaccine composition can contain other physiologically acceptable ingredients such as water, saline or a mineral oil such as DrakeolTM, MarkolTM, and squalene, to form an emulsion.

ADMINISTRATION OF POLYMER—AMTOGEN VACCINE

The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Nonlimiting examples of routes of delivery to mucosal surfaces are intranasal (or generally, the nasal associated lymphoid tissue), respiratory, vaginal, and rectal.

The dosage is determined by the antigen loading and by standard techniques for determining dosage and schedules for administration for each antigen, based on titer of antibody elicited by the polymer-antigen administration, as demonstrated by the following examples.

Although in the preferred embodiment the polymerantigen mixture is administered simultaneously, in an alternative embodiment, the polymer and antigen are administered separately to the same or nearby site. The polymer serves to attract cells of the immune system to the site, where they process the antigen.

The polyphosphazene adjuvants and methods of synthesis will be further understood by reference to the following non-limiting examples.

EXAMPLE 1

Synthesis of poly[(carboxylatophenoxy) (glycinato)phosphazene].

poly[(carboxylatophenoxy)(glycinato)phosphazene] was prepared as follows. Poly(dichlorophosphazene) (5.0, 0.0425 moles) was dissolved in 300 ml tetrahydrofuran (THF). The sodium salt of propyl p-hydroxybenzoate (prepared by reacting propyl hydroxybenzoate (30.6 g, 0.17 moles) with 60% sodium hydride (6.12, 0.15 moles) in THF) was added dropwise to the dissolved polymer. After addition of the sodium salt, the reaction mixture was stirred at reflux for 2 days and monitored by 31P NMR.

Ethyl glycinate hydrochloride (23.63 g, 0.17 moles) was suspended in 50 ml toluene containing triethylamine (23.69, 0.17 moles) and refluxed for 3.5 hours. The reaction mixture was cooled in an ice bath and triethylamine hydrochloride precipitated from the solution. The solution was filtered and added to the polymer mixture at 0° C. The reaction mixture was allowed to warm to room temperature and stirred for 2 days. The polymer was purified by repeated precipitations into 100% ethanol.

The resulting polymer (0.5 g, 1.33 mmol) was dissolved in dry THF (20 ml). The solution was added slowly to a mixture of potassium tert-butoxide and water in dry THF. For the first 5 minutes, the mixture was cooled to 0° C.; it was then stirred at room temperature for 40 hours. A large excess of ice water (300 ml) was added, and the solution was concentrated by evaporation. The polymer was isolated by acidification of the solution with hydrochloric acid to pH 5.5. The conditions of reactions and weight average molecular weights of obtained polymers measured by gel permeation chromatography in water is shown in Table 1 below.

TABLE 1

Synthesis of poly[(carboxylatophenoxy) (glycinato) phosphazene].

| No | Concentration of polymer % w/v mol/1 | Concentration of potassium tert-butoxide | Concentration of water mol/1 | Reaction time hours | MW kDa |
| --- | --- | --- | --- | --- | --- |
| 1 | 0.42 | 0.30 | 0.1 | 42 | 80 |
| 2 | 0.42 | 0.15 | 0.05 | 18 | 130 |
| 3 | 0.42 | 0.04 | 0.05 | 5 | 170 |

The structures of polymers were confirmed by $1_H$ and $31_P$ NMR (JEOL FX90Q NMR spectrometer) and elemental microanalysis.

EXAMPLE 2

Synthesis of Poly[di(carboxylatophenoxy) phosphazene].

Poly[di(carboxylatophenoxy)phosphazene] was prepared by chemical modification of poly(dichlorophosphazene) with the sodium salt of propyl p-hydroxybenzoate, followed by hydrolysis of ester groups to carboxylic acid as described in Allcock, H. R. & Kwon, S. (1989) Macromolecules 22, 75–79, the teachings of which are incorporated herein.

EXAMPLE 3

Synthesis of poly[(carboxylatophenoxy) (chloro)phosphazene].

Poly[(carboxylatophenoxy)(chloro)phosphazene] was prepared as follows. Poly[di(chloro)phosphazene] (5.0 g, 0.0425 moles) was dissolved in 300 mL tetrahydrofuran (THF). The sodium salt of propyl p-hydroxybenzoate, prepared by reacting propyl hydroxybenzoate (15.52 g, 0.0864 moles) with 60 % sodium hydride (3.06 g, 0.0765 moles) in THF, was added dropwise to the dissolved polymer. After addition of the sodium salt, the reaction mixture was stirred at reflux for 2 days and monitored by 31P NMR. The polymer was purified by repeated precipitations into water, ethanol and hexane.

Poly[(propylhydroxybenzoate) (chloro)phosphazene] (2.0 g) was dissolved in 200 mL dry THF. 20 g potassium tertbutoxide was dissolved in 200 mL THF. The basic solution was cooled to 0° C. Water (1 mL) was added to the butoxide/THF solution and stirred for 5 minutes. The polymer solution then was added dropwise to the aqueous base. The reaction mixture was warmed to room temperature and stirred for 40 hours. After 40 hours, the reaction mixture was poured over an ice-water mixture and the THF was allowed to evaporate. The aqueous solution was then dialyzed against water for 2 days. After dialysis was complete, the dialysate was acidified with HCl and the resultant white precipitate, poly[(carboxylatophenoxy) (chloro)phosphazene], containing potassium as a counterion, was washed with water and filtered from the solution.

Elemental analysis data: "P"-10.39; "N"-4.52; "C"-47.26; "Cl"-1.44, "K"-2.61.

EXAMPLE 4

Degradation of Phosphazene Polyectrolytes

Degradation of poly[(carboxylatophenoxy)(glycinato) phosphazene] was studied in vitro at 37° C. in an air gravity incubator (Imperial II Incubator, Lab-Line Instruments, Inc.), with gentle agitation on a rotating shaker (ORBIT Shaker, LabLine Instruments, Inc., Melrose Park, Ill.) in vials containing a suspension of 50 mg of polymer in 5 ml of 13 mM HEPES buffered saline solution (pH 7.4). The molecular weight of polyphosphazenes was determined by a Perkin-Elmer Series 10 liquid chromatograph with ultraviolet and a refractive index detector by using an Ultragel 2000 column (Waters Chromatography Division, Millipore Corporation, Milford, Mass.). 13 mM Hepes buffered saline solution (pH 7.4) was used as an eluant. Chromatograms were processed by GPC 5 and CHROM 2 software (Perkin-Elmer) to calculate the weight-average and number-average molecular weights using polyacrylic acid as a standard. The decline in polymer molecular weight over time is shown in Table 2.

TABLE 2

Degradation of Poly[(carboxylatophenoxy) (glycinato)phosphazene].

| Time days | Weight average molecular weight kDa | Number average molecular weight kDa |
| --- | --- | --- |
| 0 | 132.0 | 70.0 |

TABLE 2-continued

Degradation of Poly[(carboxylatophenoxy)
(glycinato)phosphazene].

| Time days | Weight average molecular weight kDa | Number average molecular weight kDa |
|---|---|---|
| 15 | 40.6 | 13.8 |
| 60 | 6.3 | 1.5 |
| 180 | 6.0 | 0.9 |
| 240 | 0.9 | 0.5 |

Degradation of poly[(carboxylatophenoxy)(chloro) phosphazene] was studied in vitro at 37° C., in an incubator-shaker (New Brunswick Scientific, G 24) in vials containing a 0.2% solution of polymer in phosphate buffered saline solution (pH 7.4). The molecular weight of polyphosphazenes was determined by a Waters chromatograph with ultraviolet (Waters 486, Millipore Corporation, Milford, Mass.) and a refractive index detector (Waters 410, Millipore Corporation, Milford, Mass.) by using an Ultragel linear column (Waters Chromatography Division, Millipore Corporation, Milford, Mass.). Phosphate buffered saline solution (pH 7.4) was used as an eluant. Chromatograms were processed by Millenium 2.0 software to calculate the weight-average and number-average molecular weights using polyacrylic and polymethacrylic acid as the standards (1,250 Da –1,100,000 Da). The decline in polymer molecular weight over time is shown in Table 3.

TABLE 3

Degradation of Poly[(carboxylatophenoxy)
(chloro)phosphazene].

| Time days | Weight average molecular weight kDa | Number average molecular weight kDa |
|---|---|---|
| 0 | 120.0 | 42.0 |
| 1 | 113.0 | 42.0 |
| 6 | 105.0 | 41.0 |
| 8 | 100.0 | 39.0 |
| 10 | 96.0 | 39.0 |
| 14 | 95.0 | 39.0 |
| 18 | 86.0 | 35.0 |
| 28 | 73.0 | 31.0 |
| 35 | 67.0 | 30.0 |
| 59 | 59.0 | 28.0 |
| 91 | 51.0 | 23.0 |

EXAMPLE 5

Antibody titers after Immunization with Tetanua Toxoid Admixed with Polyphosphazene Adjuvant.

Antibody titers were determined in female BALB/c mice, age 7 to 8 weeks, that had been inoculated with tetanus toxoid admixed with various concentrations of polyphosphazene adjuvant.

An immunogenic composition containing tetanus toxoid in polyphosphazene was prepared as follows. 100 mg of poly[di(carboxylatophenoxy)phosphazene] was dissolved in 1 ml $Na_2CO_3$ and 1 ml phosphate buffered saline (PBS), pH 7.2 was added. 1.4 ml tetanus toxoid (2.2 mg/ml or 1000 LF/ml, Connaught Laboratories, Inc., Swiftwater, Pa.) was added with 0.6 ml containing 0.025% Brij solution (10 ul of 10% Brij 58, Sigma Chemical Co., St. Louis, Mo.) to the polymer. Groups of five mice were immunized subcutaneously with a single dose of 25 ug tetanus toxoid admixed with dilutions containing 0.5% polyphosphazene, 0.05% polyphosphazene, or 0.005% polyphosphazene in $dH_2O$. A separate group of mice was immunized with a single subcutaneous dose of 25 ug of tetanus toxoid in complete Freund's adjuvant (SIGMA, St. Louis, Mo.). Blood samples were taken from the retroorbital sinus of $CO_2$ anaesthetized mice and analyzed by an ELISA immunoassay for anti-tetanus toxoid IgG.

As shown in Table 4, the antigen polymer solution elicited in a dose dependent manner anti-tetanus toxoid ELISA antibodies. 0.5% PCPP enhanced the immune response to tetanus toxoid more than 100 fold compared to the response to tetanus toxoid in water. PCPP at 0.05% and 0.005% concentrations also elicited higher antibody titers than tetanus toxoid in water, although not as high as what was obtained with 0.5% PCPP. Furthermore, the 0.5% PCPP concentration was as strong an adjuvant as complete Freund's adjuvant.

Another immunogenic composition containing various doses of tetanus toxoid in polyphosphazene was prepared as follows. 100 mg of poly[di(carboxylatophenoxy) phosphazene] was dissolved in 1 ml $Na_2CO_3$ and 1 ml phosphate buffered saline (PBS), pH 7.6 was added. Subsequently, tetanus toxoid (2.2 mg/ml) (Connaught Laboratories, Swiftwater, Pa.) was diluted 1:10 in water and the appropriate volume was admixed with 0.1% polyphosphazene.

Groups of three mice were immunized subcutaneously with a single dose of each immunogenic composition. Blood samples were taken from the retroorbital sinus of $CO_2$ anaesthetized mice after 21 days after inoculation and analyzed by an ELISA immunoassay for anti-tetanus toxoid IgG (Table 5). As expected there was a clear antigen dose dependent response at all time points using soluble PCPP. The 25 ug tetanus toxoid dose formulated into 0.1% PCPP elicited ELISA titers that were dramatically higher than the same amount of antigen in water and compared very favorably with 25 ug of tetanus toxoid in complete Freund's adjuvant. It should be noted that at the 5, 1, and 0.2 ug antigan dose levels in PCPP the ELISA titers were still rising at week 25, whereas with the complete Freund's adjuvant formulation the ELISA titers had peaked earlier.

EXAMPLE 6

Antibody Titers after Immunization with Influenza Virus Admixed with a Polyphosphazene Adjuvant.

An immunogenic composition containing influenza virus influenza (Influenza Branch, Center for Disease Control, Atlanta, Ga.) and 0.1% PCPP was formulated. Influenza was grown in eggs according to standard methods and quantitated by protein, haemagglutination and plaque assays. Influenza was formalin inactivated by the addition of a 38% formaldehyde solution at a final dilution of 1:4000.

The following influenza immunoassay protocol was performed to determine the influenza titers: 96-well ELISA microtiter plates were coated with influenza cell lysates at 10 ug/ml in carbonate buffer, pH 9.6, 100 ml per well and incubated 2 hours at 37° C. The plate was washed with 0.05% Tween 20/PBS (Sigma, St. Louis, Mo.) and 100 ul 2.5% bovine serum albumin/phosphate buffered saline (BSA/PBS) was added to each well as a blocking step. The plate was then incubated 1 hour at 37° C. and washed with 0.05% Tween 20/PBS. 50 ul 1% BSA/PBS was added to all wells. Serum samples were diluted to 1:128 by adding 5 ul serum to 635 ul 1% BSA/PBS. 50 ul of the dilute serum sample to be assayed was added to the first well in a row, a 1:256 dilution. Both positive and negative controls were tested. Two-fold serial dilutions of serum sample were made by removing 50 ul from the first well in a row and adding the 50 ul with mixing to the second well; then removing 50 ul from the second well and adding it to the third well with mixing, and so on down the row, discarding 50 ul from the final or 12th well. The plates were then incubated 1 hour at 37° C. and the plate washed with 0.05% Tween 20/PBS. To each well was added 100 ul of OPD solution (0.4 mg/ml solution of 0-phenylenediamine dihydrochloride (Sigma, St. Louis, Mo.) in 0.05M phosphate-citrate buffer pH 5.0 (1 OPD tablet per 12.5 ml citrate buffer) containing 0.05% hydrogen peroxide (20.8 ul 30% H2O2 per 12.5 ml citrate buffer)). The color was allowed to develop for 30 minutes, then stopped by addition of 50 µl 2M H2SO4/ well. The absorbance was read at $OD_{490}$, and the endpoint titer determined by finding the dilution of each serum sample that had an $OD_{490}$ greater than or equal to two times the $OD_{490}$ of the negative control at the same dilution.

The influenza hemagglutination inhibition antibody assay was done with heat-inactivated mouse serum that has been incubated for 30 minutes with 10% chicken red blood cells (Spafas) to remove non-specific inhibitors. Twofold dilutions of sera were added to a 96 well microtiter plate and 8 HA units of virus suspension in an equal volume were added to each well and incubated at room temperature for 30 minutes. A 0.5% suspension of chicken red blood cells was added to each well and incubated at room temperature for 45–60 minutes. The HAI titers are expressed as the reciprocal of the highest dilution that completely inhibits hemagglutination of erythrocytes.

The induction of influenza antigen specific neutralizing antibodies was measured by plaque reduction. This assay measures the amount of antibody resulting in a 50% reduyction in influenza infectivity in cell culture. Serum samples were heat inactivated at 56° C. for 30 minutes. Twofold dilutions of serum were made beginning at 1:50 in DMEM (JRH Biochemicals) and 0.5 ml of each dilution was added to 0.5 ml of influenza virus at a titer of 400 pfu/ml. After incubation at 37° C. for 1 hour, 250 µl of each sample was allowed to absorb to a confluent monolayer of MDCK cells for 1 hour. The adsorption mix was aspirated off, and the cells were overlayed with a MEM/0.6% agarose mixture containing 10 µg/ml trypsin. Plaques were visible after 3 days. The agarose plugs were removed, and the monolayers stained with crystal violet(J. J. Baker). Plaques were counted, and a 50% reduction in titer is determined by comparing to 50% of the number of plaques in a control infection containing no serum.

Mice were inoculated subcutaneously with varying influenza doses formulated in 0.1% PCPP or 5 µg of influenza in water or complete Freund's adjuvant. As expected there was a dose dependent ELISA immune response (Table 6) at all time points after inoculation with the 0.1% PCPP formulated influenza antigen. In this experiment, 5 ug of influenza in 0.1% polyphosphazene induced a dramatically higher anti-influenza response than 5 ug of influenza in Complete Freund's Adjuvant. Furthermore, all antigen doses in the PCPP formulation elicited an immune response that was still rising at week 25 whereas the complete Freund's adjuvant formulation induced peak titers at earlier time points. This is similar to the results seen in the tetanus toxoid experiments. It is particularly noteworthy that the 0.04 ug dose in PCPP did not induce detectable antibody levels until week 25. This can be interpreted as evidence for sustained release of antigen.

The ability of 0.1% PCPP solution to induce functional antibodies was assayed in hemagglutination inhibition (Table 7) and neutralization (Table 8) assays. Once again, the PCPP formulation induced very high antibody activities in the hemagglutination and neutralization assays whereas there was little or no activity detectable in these assays in complete Freund's adjuvant formulations.

The influenza vaccine is administered to humans without alum because this adjuvant has very little positive effect on the immune response. In a mouse potency test, an antigen dose that induces HAI antibody titers $\geq 40$ units is predictive of protection in a human. Thus, 0.04 ug of total influenza antigen in 0.1% PCPP was able to induce protective levels of antibody that were not achieved with 5 ug of unadjuvanted antigen The antibody isotypes engendered in this response were also assayed (Table 9). Although the PCPP formulated influenza antigen induced largely an IgG1 response, significant IgG2a and 2b responses were also detected. The level of this response was greater than what was observed for complete Freund's adjuvant formulated influenza antigens. No IgG3antibodies were detectable in this experiment.

EXAMPLE 7

Antibody Titers after Immunization with H. influenzas Type b Polysaccharide Antigen Admixed with a Polyphosphazene Adjuvant.

All of the antigens discussed in the foregoing have been protein antigens. We next investigated the immunogenicity of the PRP polysaccharide derived from Haemophilus influenza type B (Hib). Polysaccharide antigens normally do not give an IgG response with memory unless they are conjugated to a protein antigen. Hib conjugated to tetanus toxoid was formulated with either alum or 0.1% PCPP (Table 10). Mice were injected subcutaneously with 2 µg of PRP in either the alum or PCPP formulations. The antibody response was followed by determining the specific anti-PRP IgG levels at each time point. The alum adjuvanted immunogen elicited detectable antibody levels at the four week time point and elicited peak titers at week eight. There followed a rapid decrease of the antibody titers extending out to week 20. PCPP adjuvanted Hib antigen elicited 6 fold higher antibody levels at the four week time point than were seen with alum. PCPP adjuvanted antigen also elicited peak titers at week 8, but these titers were approximately ten fold higher than what was achieved with alum. Although the PCPP adjuvanted antibody titers decreased over the following weeks, they were still 2 fold higher at week 20 than what was achieved with the alum at the peak 8 week time point.

EXAMPLE 8

Antibody Titers after Immunization with Tetanus Toxoid Antigen Admixed with Polyelectrolytes.

We compared the effect of PCPP with the effect achieved with two other polyelectrolytes, polymethylacrylic acid (PMA) and polyacrylic acid (PAA). Mice were injected with 1µg of TT formulated into 0.1% solutions of the polymers. The anti-TT ELISA titers were determined at weeks 3, 6 and 9. It is apparent from the data compiled in Table 11 that 0.1% PCPP stimulated a higher antibody response than what was seen with any of the molecular weights of PMA and PAA. It should be noted that there is some tendency for the antibody response to rise as the molecular weight of the PMA and PAA polymers increase. Nevertheless, 0.1% PMA having a molecular weight of 1.3 million daltons was unable to stimulate an immune response equivalent to 0.1% PCPP.

EXAMPLE 9

Antibody Titers after Immunization with Influenza Antigan Admixed with a Polyphosphazene of Various Molecular Weights.

The PCPP solutions used in the experiments described in the above examples were polydispersed containing molecules ranging from 2,000 to circa 10,000,000 daltons. It was, therefore, of interest to examine the effect of PCPP molecular weight on the adjuvant property. PCPP was fractionated by sequential acid precipitation and FPLC column chromatography to acquire PCPP fractions having relatively narrow polydispersities (ranging from 1.37–2.01) and peak average molecular weights ranging from 3,000–1.8 Million. The HPLC analysis of these fractions is shown in Table 12. 0.1% concentrations of each of these fractions were mixed with 5µg of formalin inactivated influenza virus and injected subcutaneously into mice. An admixture of equal volumes of each one of these formulations was also prepared such that the final PCPP concentration was 0.1% and the amount of inactivated influenza virus was 5µg. Mice were injected with this PCPP recombined formulation. As a control, another group of mice were injected with influenza formulated into 0.1% unfractionated PCPP. The data shown in Table 13 demonstrate the positive correlation between increasing PCPP molecular weights and increasing antibody responses to the influenza antigen. The response elicited by the 0.1% PCPP having a molecular weight of 1.8 Million was essentially indistinguishable from the PCPP formulations of recombined fractions and the unfractionated PCPP.

EXAMPLE 10

Antibody Titers after Immunization with Tetanus Toxoid or Influenza Admixed with Various Concentrations of Three Different Phosphazene Polymer Adjuvants.

100 mg of Poly[di(carboxylatophenoxy)phosphazene] (Polymer 1), poly[(carboxylatophenoxy) (glycinato)phosphazene] (Polymer 2) or poly[(carboxylatophenoxy) (chloro)phosphazene] (Polymer 3) were dissolved in 1 ml Na$_2$CO$_3$ and 3 ml of PBS was added to the polymer solution.

Antibody titers were determined in groups of female BALB/c mice, three mice per group, age 7 to 8 weeks, after subcutaneous injection with 5 µg influenza admixed with Polymer 1 or Polymer 2. As shown in Table 14, flu in of Polymer 1 or Polymer 2 elicited serum IgG titers that were as high or higher than the same dosage of antigen in complete Freund's adjuvant. These serum IgG titers were maintained 21 weeks after immunization Antibody titers were determined in groups of female BALB/c mice, three mice per group, age 7 to 8 weeks, after subcutaneous injection with 1 ug tetanus toxoid admixed with Polymer 1 or Polymer 3. As shown in Table 15, tetanus toxoid in polymer 1 or polymer 3 induced serum IgG titers that were maintained 25 weeks after immunization.

TABLE 4

ELISA Antibody Titers After Administration of Tetanus Toxoid Admixed with Various Concentrations of Polyphosphazene Adjuvant or Freund's adjuvant

| | anti- TT ELISA titer at week | | | |
|---|---|---|---|---|
| | 3 | 5 | 7 | 9 |
| TT in water | 1024 | 2048 | 2048 | 4096 |
| TT/0.5% PCPP | 65536 | 262144 | 524288 | 524288 |
| TT/0.05% PCPP | 16384 | 32768 | 32768 | 65536 |
| TT/0.005% PCPP | 4096 | 8192 | 32768 | 32768 |
| TT/CFA | 16384 | 131072 | 262144 | 262144 |

Mice were immunized with 25 µg of tetanus toxoid (TT).

TABLE 5

ELISA Antibody Titers After Administration of Various Doses of Tetanus Toxoid Admixed with a Polyphosphazene Adjuvant or Freund's adjuvant

| | anti- TT ELISA titer at week TT | | | | |
|---|---|---|---|---|---|
| | 3 | 6 | 9 | 17 | 25 |
| 25 µgTT/0.1% PCPP | 16384 | 65536 | 131072 | >524288 | 262144 |
| 5 µgTT/0.1% PCPP | 4096 | 16384 | 32768 | 65536 | 131072 |
| 1 µgTT/0.1% PCPP | 2048 | 16384 | 16384 | 32768 | 65536 |
| 0.2 µgTT/0.1% PCPP | 512 | 1024 | 1024 | 2048 | 4096 |
| 25 µg TT in water | 2048 | 2048 | 8192 | 8192 | 16384 |
| 25 µg TT in CFA | 16384 | 131072 | 262144 | 131072 | 131072 |

TABLE 6

ELISA Antibody Titers After Administration of Influenza Admixed with a Polyphosphazene Adjuvant or Freund's adjuvant

| | anti- TT ELISA titer at week week | | | | | |
|---|---|---|---|---|---|---|
| | 3 | 6 | 9 | 17 | 25 | 37 |
| 5 µg flu/0.1% PCPP | 2048 | 16384 | 16384 | 32768 | 65536 | 16384 |
| 1 µg flu/0.1% PCPP | 4096 | 16384 | 16384 | 21768 | 131072 | 16384 |
| 0.2 µg flu/0.1% PCPP | <256 | 4096 | 4096 | 16384 | 65536 | 8192 |
| 0.05 µg flu/0.1% PCPP | <256 | <256 | <256 | <256 | 4096 | 1024 |
| 5 µg flu in water | 256 | 256 | 256 | <256 | <256 | <256 |
| 5 µg flu in CFA | 512 | 4096 | 4096 | 2048 | 1024 | 2048 |

TABLE 7

Hemagglutination Inhibition Antibody Titers After Administration of Influenza Admixed with a Polyphosphazene Adjuvant or Freund's adjuvant

| | HAI titer at week | | | | | |
|---|---|---|---|---|---|---|
| | 3 | 6 | 9 | 17 | 25 | 37 |
| 5 μg flu/0.1% PCPP | 160 | 1280 | 1280 | 2560 | 640 | 1280 |
| 1 μg flu/0.1% PCPP | 320 | 1280 | 1280 | 2560 | 2560 | 1280 |
| 0.2 μg flu/0.1% PCPP | 40 | 640 | 640 | 2560 | 1280 | 1280 |
| 0.05 μg flu/0.1% PCPP | neg | 40 | 80 | 160 | 160 | 160 |
| 5 μg flu in water | neg | neg | 20 | neg | neg | neg |
| 5 μg flu in CFA | neg | 80 | 40 | 40 | 40 | 40 |

TABLE 11

ELISA Antibody Titers After Administration of Tetanus Toxoid Admixed with Polyelectrolytes

| | anti-flu ELISA titer at week | | |
|---|---|---|---|
| | 3 | 6 | 9 |
| TT/PBS | 512 | 512 | 256 |
| TT/CFA | 4096 | 4096 | 4096 |
| TT/0.1% PCPP | 16384 | 16384 | 65536 |
| TT/0.1% PMA MW 7,000 | 1024 | 1024 | 1024 |
| TT/0.1% PMA MW 25,000 | 512 | 512 | 512 |
| TT/0.1% PMA MW 70,000 | 512 | 1024 | 1024 |
| TT/0.1% PMA MW 110,000 | 512 | 1024 | 1024 |
| TT/0.1% PMA MW 350,000 | 1024 | 1024 | 512 |

TABLE 8

Plaque Neutralization Antibody Titers After Administration of Influenza Admixed with a Polyphosphazene Adjuvant or Freund's adjuvant

| | HAI titer at week | | | | | |
|---|---|---|---|---|---|---|
| | 3 | 6 | 9 | 17 | 25 | 37 |
| 5 μg flu/0.1% PPP | 200 | 400 | 400 | 200 | 400 | 1600 |
| 1 μg flu/0.1% PPP | 400 | — | 200 | 400 | 400 | 400 |
| 0.2 μg flu/0.1% PPP | <100 | — | too | 100 | 400 | 400 |
| 0.05 μg flu/0.1% PPP | <100 | — | <100 | <100 | — | <100 |
| 5 μg flu in water | <100 | <100 | <100 | <100 | — | <100 |
| 5 μg flu in CFA | <100 | <100 | <100 | <100 | — | <100 |

TABLE 9

Influenza Specific Antibody Isotypes After Administration of Influenza Admixed with a Polyphosphazene Adjuvant or Freund's adjuvant

| | Antibody isotype titer at week | | | | | | | | |
|---|---|---|---|---|---|---|---|---|---|
| | 3 | | | 6 | | | 9 | | |
| | IgG1 | IgG2A | IgG2B | IgG1 | IgG2A | IgG2B | IgG1 | IgG2A | IgG2A |
| 5 μg flu/0.1% PCPP | 8192 | <256 | <256 | 131072 | <256 | 256 | 131072 | 256 | 1024 |
| 1 μg flu/1% PCPP | 8192 | <256 | <256 | 65536 | 256 | 1024 | 65536 | 1024 | 4096 |
| 0.2 μg flu/0.1% PCPP | 256 | <256 | <256 | 16384 | 1024 | 2048 | 16394 | 1024 | 1024 |
| 5 μg flu/water | <256 | 1024 | <256 | 256 | 1024 | <256 | 256 | 512 | <256 |
| 5 μg flu/CFA | 2048 | <256 | <256 | 16384 | 1024 | 512 | 16384 | 1024 | 256 |

All samples had IgG3 antibody titers <256.

TABLE 10

ELISA Antibody Titers After Administration of H. influenza Type b Polysaccharide Admixed with a Polyphosphazene Adjuvant or Alum adjuvant
Anti-PRP IgG(μg/ml)

| Alum | | | | | Polyphosphazene | | | | |
|---|---|---|---|---|---|---|---|---|---|
| wk 4 | wk 8 | wk 12 | wk 16 | wk 20 | wk 4 | wk 8 | wk 12 | wk 16 | wk 20 |
| 5.48 | 10.00 | 5.97 | 5.45 | 3.84 | 32.16 | 109.31 | 50.80 | 35.51 | 18.60 |

*Geometric Mean Titer of 10 mice
Immunization dose = 2 μg PRP per mouse

TABLE 11-continued

ELISA Antibody Titers After Administration of Tetanus Toxoid Admixed with Polyelectrolytes

|  | anti-flu ELISA titer at week | | |
|---|---|---|---|
|  | 3 | 6 | 9 |
| TT/0.1% PAA MW 2,000 | 1024 | 512 | 512 |
| TT/0.1% PAA MW 35,000 | 512 | 512 | 1024 |
| TT/0.1% PAA MW 500,000 | 4096 | 4096 | 4096 |
| TT/0.1% PMA MW 1,300,000 | 4096 | 4096 | 4096 |

TABLE 12

Molecular Weights and Polydispersities of Fractionated Polyphosphazene Determined on HPLC Polyphosphazene Fractionation-HPLC

| Peak Average Molecular Weight | Polydispersity |
|---|---|
| 3,000 | 1.62 |
| 25,500 | 1.37 |
| 72,000 | 1.54 |
| 331,000 | 1.64 |
| 464,000 | 1.57 |
| 634,000 | 1.56 |
| 1,846,000 | 2.01 |

TABLE 13

ELISA Antibody Titers After Administration of Influenza Admixed with a Polyphosphazene of Various Molecular Weights

| PBS | <64 | PCPP MW 464 | <64 |
|---|---|---|---|
|  | 128 |  | 512 |
|  | <64 |  | 256 |
|  | <64 |  | 256 |
|  | <64 | 512 |  |
| PCPP MW 3,000 | <64 | PCPP MW 634,6000 | 512 |
|  | <64 |  | 512 |
|  | <64 |  | 1024 |
|  | <64 |  | 1024 |
|  | <64 |  | 1024 |
| PCPP MW 25,500 | 256 | PCPP MW | 1024 |
|  | <64 | 1,846,000 | 1024 |
|  | <64 |  | 2048 |
|  | 128 |  | 8192 |
|  | <64 |  | 4096 |
| PCPP MW 72,000 | <64 | PCPP Fractions | 51 |
|  | <64 | Recombined | 1024 |
|  | <64 |  | 2048 |

TABLE 13-continued

ELISA Antibody Titers After Administration of Influenza Admixed with a Polyphosphazene of Various Molecular Weights

|  | <64 |  | 2048 |
|---|---|---|---|
|  | 256 |  | 128 |
| PCPP MW 331,000 | 256 | PCPP | 8192 |
|  | <64 | Unfractionated | 2048 |
|  | 128 |  | 8182 |
|  | 2048 |  | 2048 |
|  | 256 |  | 2048 |

Mice were immunized with 5 μg formalin inactivated influenza virus per dose. All PCPP solutions were administered as 0.1% concentrations.

TABLE 14

ELISA Antibody Titers After Administration of Influenza Admixed with Poly[di(carboxylatophenoxy) phosphazene] (Polymer 1), Poly[(carboxylatophenoxy)(glycinato)phosphazene] (Polymer 2) or Freund's adjuvant

|  | anti-flu ELISA titer at week | | | | | | |
|---|---|---|---|---|---|---|---|
|  | 3 | 5 | 7 | 9 | 13 | 17 | 21 |
| Flu in 0.1% in Polymer | 14096 | 8192 | 65535 | 32768 | 8192 | 32768 | 32768 |
| Flu in 0.1% in Polymer | 21024 | 1024 | 4096 | 2048 | 1024 | 4096 | 4096 |
| Flu Complete Freund's | 256 | 1024 | 16384 | 1024 | 512 | 4096 | 4096 |

Mice were immunized subcutaneously 5 μg whole formalin inactivated influenza virus particles

TABLE 15

ELISA Antibody Titers After Administration of Tetanus Toxoid Admixed with Poly[di(carboxylato phenoxy)phosphazene] (Polymer 1) or Poly[(carboxylatophenoxy)(chloro)phosphazene] (Polymer 3)

|  | anti-flu ELISA titer at week | | | | | | |
|---|---|---|---|---|---|---|---|
|  | 3 | 6 | 9 | 13 | 17 | 21 | 25 |
| TT in 0.1% in Polymer | 14096 | 2048 | 4096 | 4096 | 8192 | 16384 | 16384 |
| TT in 0.1% in Polymer | 32048 | 512 | 2048 | 1024 | 1024 | 2048 | 2048 |

Mice were immunized subcutaneously 1 μg TT.

Modifications and variations of the present invention, polymer adjuvants and methods of synthesis and use in vaccine compositions, will be obvious to those skilled in the art from the foregoing detailed description. Such modifications and variations are intended to come within the scope of the appended claims.

We claim:

1. A method for producing an immune response in an animal comprising:

producing an immune response in an animal by administering to the animal an antigen and a polyphosphazene polyelectrolyte adjuvant in an amount effective to elicit an immune response in the animal against said antigen, said polyphosphazene being at least partially soluble in water.

2. The method of claim 1 wherein the antigen and polyphosphazene are first combined and the combination is administered to the animal.

3. The method of claim 1 wherein said administering is a parenteral administration.

4. The method of claim 1 wherein the polyphosphazene contains carboxylatophenoxy pendant groups.

5. The method of claim 1 wherein the polyphosphazene is a copolymer which comprises poly [di(carboxylatophenoxy)phosphazene].

6. The method of claim 1 wherein the polyphosphazene polymer is poly [di(carboxylatophenoxy)phosphazene-co-di(chloro)phosphazene-co-(carboxylatophenoxy)(chloro)phosphazene)].

7. The method of claim 1 wherein the polyphosphazene polyelectrolyte contains hydrolyzable side chains selected from the group consisting of amino acid, amino acid ester, chlorine, imidazole, glycerol, and glucosyl.

8. The method of claim 1 wherein the polyphosphazene polyelectrolyte is cross-linked by a multivalent cation.

9. The method of claim 1 wherein the polyphosphazene polyelectrolyte is physically mixed with the antigen.

10. The method of claim 1 wherein the antigen is selected from the group consisting of proteins, peptides, polysaccharides, glycoproteins, and glycolipids.

11. The method of claim 1 wherein the antigen is selected from the group consisting of influenza proteins, hepatitis B proteins, bacterial proteins and bacterial lipopolysaccharides.

12. The method of claim 3 wherein the polyphosphazene contains carboxylatophenoxy pendant groups.

13. The method of claim 9 wherein said administering is a parenteral administration.

14. The method of claim 1 wherein the polyphosphazene has a molecular weight in excess of 1000.

15. The method of claim 1 wherein the ratio of antigen to polyphosphazene is from 0.5:1 to 0.0001:1.

16. The method of claim 15 wherein the polyphosphazene has a molecular weight in excess of 1000.

17. The method of claim 14 wherein the polyphosphazene is a copolymer which comprises poly [di(carboxylathophenoxy)phosphazene].

18. The method of claim 15 wherein the polyphosphazene is a copolymer which comprises poly [di(carboxylathophenoxy)phosphazene].

* * * * *